(12) United States Patent
Rautenberg et al.

(10) Patent No.: US 10,605,779 B2
(45) Date of Patent: Mar. 31, 2020

(54) METHOD FOR DETERMINING PROPERTIES OF A MEDIUM AND DEVICE FOR DETERMINING PROPERTIES OF A MEDIUM

(71) Applicant: SENSACTION AG, Coburg (DE)

(72) Inventors: Jens Rautenberg, Geseke (DE); Rudolf Braun, Ahorn (DE); Achim Stark, Doerfles Esbach (DE); Stefan Rueger, Coburg (DE)

(73) Assignee: SENSACTION AG, Coburg (DE)

( * ) Notice: Subject to any disclaimer, the term of this patent is extended or adjusted under 35 U.S.C. 154(b) by 559 days.

(21) Appl. No.: 15/043,428

(22) Filed: Feb. 12, 2016

(65) Prior Publication Data

US 2016/0238570 A1     Aug. 18, 2016

(30) Foreign Application Priority Data

Feb. 16, 2015   (DE) .................. 10 2015 102 200

(51) Int. Cl.
*G01N 29/02* (2006.01)
*G01N 29/024* (2006.01)

(52) U.S. Cl.
CPC ..... *G01N 29/024* (2013.01); *G01N 2291/011* (2013.01); *G01N 2291/022* (2013.01); *G01N 2291/02818* (2013.01); *G01N 2291/0423* (2013.01); *G01N 2291/0426* (2013.01); *G01N 2291/0427* (2013.01); *G01N 2291/105* (2013.01)

(58) Field of Classification Search
CPC .................................................. G01N 29/024

USPC ......................................................... 73/597
See application file for complete search history.

(56) References Cited

U.S. PATENT DOCUMENTS

| | | |
|---|---|---|
| 3,575,050 A | 4/1971 | Lynnworth |
| 3,935,735 A | 2/1976 | Lee |
| 4,183,244 A | 1/1980 | Kohno et al. |
| 5,052,230 A | 10/1991 | Lang et al. |
| 6,062,091 A | 5/2000 | Baumoel |
| 6,390,999 B1 | 5/2002 | Zscheile et al. |
| 6,435,037 B1 | 8/2002 | Doten |

(Continued)

FOREIGN PATENT DOCUMENTS

| | | |
|---|---|---|
| CN | 101373951 A | 2/2009 |
| CN | 201828295 U | 5/2011 |

(Continued)

OTHER PUBLICATIONS

DE Office Action in application No. 10 2015 102 200.1 dated Aug. 7, 2019.

*Primary Examiner* — Tarun Sinha
(74) *Attorney, Agent, or Firm* — Maschoff Brennan

(57) ABSTRACT

A method for determining physical and/or chemical properties of a medium on the basis of at least one first and one second acoustic wave, which each have at least partly propagated through the medium from at least one transmitter to at least one receiver, is provided. From receive signals generated at least two receivers a runtime difference of the acoustic waves and/or an absolute runtime of an acoustic wave is determined and by means of a determined runtime difference and/or a determined absolute runtime physical and/or chemical properties of the medium are determined, such as for example a mean flow velocity.

27 Claims, 4 Drawing Sheets

(56) References Cited

U.S. PATENT DOCUMENTS

| | | |
|---|---|---|
| 6,435,038 B1 | 8/2002 | Nam |
| 6,877,387 B1 | 4/2005 | Certon et al. |
| 2002/0143479 A1 | 10/2002 | Fukuhara |
| 2006/0052963 A1 | 3/2006 | Shkarlet |
| 2009/0276167 A1 | 11/2009 | Glaser et al. |
| 2010/0288055 A1 | 11/2010 | Mueller et al. |
| 2012/0266676 A1 | 10/2012 | Mueller et al. |
| 2012/0271568 A1* | 10/2012 | Wilson .................. G01F 1/66 702/48 |
| 2014/0012518 A1 | 1/2014 | Ramamurthy et al. |
| 2015/0279072 A1* | 10/2015 | Black .................. G06T 11/60 382/109 |

FOREIGN PATENT DOCUMENTS

| | | |
|---|---|---|
| CN | 104236647 A | 12/2014 |
| DE | 1958235 A1 | 6/1970 |
| DE | 2539263 A1 | 3/1976 |
| DE | 3046254 A1 | 7/1982 |
| DE | 2832835 C2 | 3/1985 |
| DE | 3347420 C2 | 3/1987 |
| DE | 3734635 C2 | 6/1989 |
| DE | 3823177 A1 | 1/1990 |
| DE | 19818053 A1 | 10/1998 |
| DE | 19843806 A1 | 3/2000 |
| DE | 10206134 A1 | 8/2002 |
| DE | 10036732 C2 | 12/2003 |
| DE | 69907913 T2 | 5/2004 |
| DE | 19957905 B4 | 4/2005 |
| DE | 102005015456 A1 | 10/2006 |
| DE | 102008043956 A1 | 5/2010 |
| DE | 102009003020 A1 | 11/2010 |
| DE | 102009049067 A1 | 4/2011 |
| DE | 102010063937 A1 | 6/2012 |
| DE | 102012212901 A1 | 1/2014 |
| EP | 2069775 A2 | 6/2009 |
| WO | 2008/034878 A2 | 3/2008 |
| WO | 2010034713 A2 | 4/2010 |
| WO | 2012123673 A1 | 9/2012 |
| WO | 2014/016159 A1 | 7/2013 |

* cited by examiner

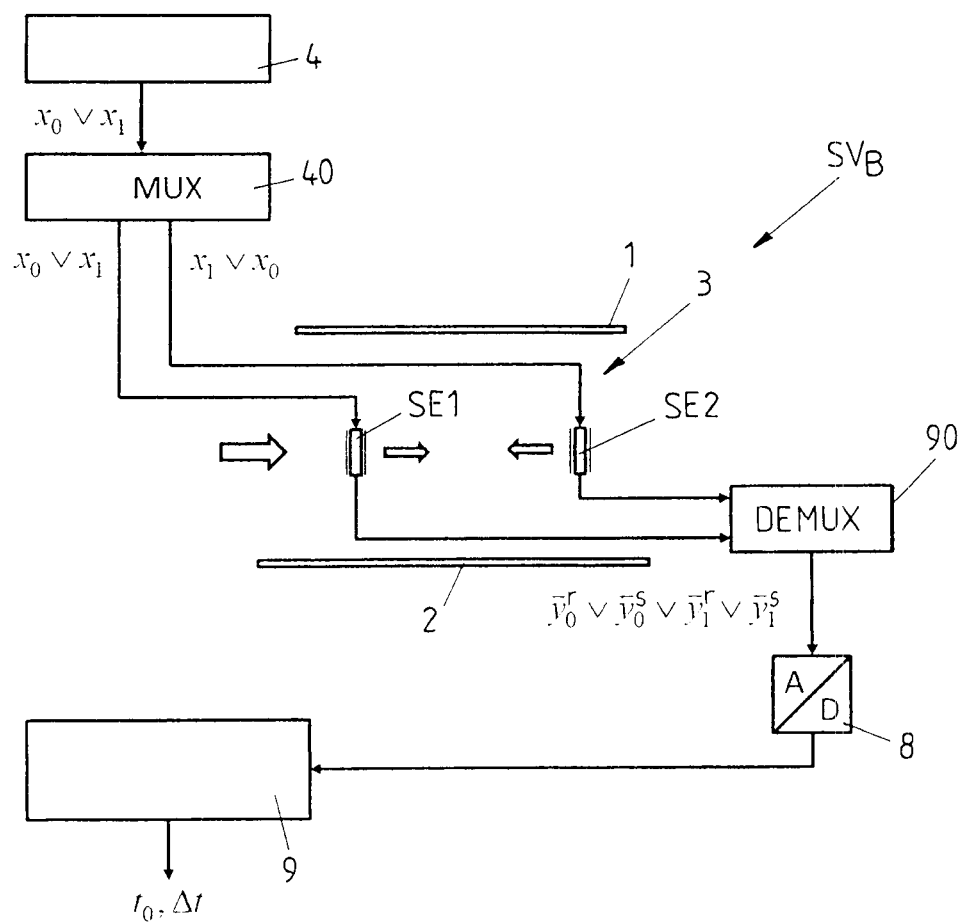

METHOD FOR DETERMINING PROPERTIES OF A MEDIUM AND DEVICE FOR DETERMINING PROPERTIES OF A MEDIUM

REFERENCE TO RELATED APPLICATION

This application claims the benefit of German Patent Application No. 10 2015 102 200.1 filed on Feb. 16, 2015 and is fully incorporated herein by reference.

BACKGROUND

The present invention relates to a method for determining physical and/or chemical properties of a medium with reference to at least one first and one second acoustic wave, which each have at least partly propagated through the medium from a transmitter to a receiver and to a device for determining physical and/or chemical properties of a medium.

The medium whose physical and/or chemical properties are to be determined by a generic method preferably is a liquid or a soft material, in particular a highly viscous, dough-like or pasty medium. The acoustic waves utilized for determining the properties for example are ultrasonic waves which are generated by a corresponding transmitter due to a transmit signal.

In a generic method, at least two acoustic waves usually are generated by a transmit signal, which at least partly propagate through the medium along identical or different propagation directions, before they each are received at a receiver located in the respective propagation direction. In a flowing medium, for example, acoustic waves on the one hand are generated in a first propagation direction in flow direction of the medium and on the other hand in a second propagation direction against the flow direction of the medium. From the receive signals generated at the respective receivers, a runtime difference then can be determined and e.g. the (mean) flow velocity of the medium can be inferred therefrom. When absolute runtimes of an acoustic wave from a transmitter to a receiver alternatively or in addition are determined by means of the receive signals, further conclusions about physical and/or chemical properties of the medium can be drawn, such as e.g. about its density, temperature or composition.

From WO 2008/034878 A2 a generic device is known, in which surface acoustic waves are generated, which in a waveguide couple volumetric sound waves into the respective medium. By repeatedly coupling surface waves out at those points at which the volumetric sound wave impinges on a wall bordering the medium, surface acoustic waves in turn are received at a receiver, whose runtimes and runtime differences are characteristic for the medium as well as its physical and/or chemical properties.

In a device described in WO 2008/034878 A2 and in the method realized therewith, the processing of the receive signals generated at the respective receivers for a received acoustic wave—here a surface acoustic wave—is of decisive importance. The determination of a runtime difference or an absolute runtime from the receive signals generated at the receivers by no means is trivial and possibly involves a considerable calculation effort. Depending on the information to be extracted from the receive signals, a variety of different methods is used for signal processing. It is known, for example, to utilize modulated transmit signals, in order to be able to more reliably infer the properties of the medium with reference to the receive signals obtained. For example, there is used a quadrature amplitude modulation, briefly IQ modulation, with which a distinct improvement of the achievable resolution also can regularly be achieved as compared to non-modulated transmit signals.

Further known methods mostly are based on sampled and analog-to-digital converted receive signals, wherein correlation functions, but also the Hilbert and Wavelett transforms are formed.

DE 102 06 134 A1 furthermore discloses a method for determining a flow velocity of a medium by means of ultrasonic waves, which should be resistant to disturbances, such as noise, during signal processing. For this purpose, generated analog receive signals are digitized, a cross correlation is carried out, and a Hilbert conversion is performed, in order to calculate a phase relation between received acoustic waves and therefrom a time difference. A suitable device for processing the receive signals (signal processing device) thus is comparatively complex, however, and hence involves considerable costs.

SUMMARY

Proceeding therefrom, it is an object underlying the present invention to provide an improved method for the determination of physical and/or chemical properties of a medium by means of acoustic waves, which is improved with regard to the calculation effort during signal processing of the receive signals and in particular provides for a particularly reliable and robust as well as inexpensive determination of a flow velocity of a medium by means of acoustic waves. Furthermore, a device for carrying out this method should be provided.

This object is solved with the methods as described herein and with the device as described herein.

The methods proceed from a determination of a runtime difference between received acoustic waves and acoustic waves propagating along identical and/or different propagation directions and a determination of an absolute runtime of an acoustic wave from at least one transmitter to at least one receiver, wherein an acoustic wave always has at least partly propagated through the medium to a receiver. The methods according to the invention of course also can easily be combined with each other, so that e.g. after the determination of an absolute runtime and a known distance of transmitter and receiver the sound velocity of the acoustic waves in the medium can be inferred and a proportionality factor then is available, which together with a determined runtime difference can be utilized for the calculation of a (mean) flow velocity of the flowing medium.

The methods each proceed from the fact that at least one first and one second acoustic wave have at least partly propagated through the medium from a transmitter to a receiver, and the acoustic waves each are generated by a transmit signal, the first acoustic wave propagates through the medium along a first propagation direction and the second acoustic wave propagates through the medium along a second propagation direction preferably different from the first propagation direction, e.g. opposite to the same, and for a received first acoustic wave a first receive signal is generated after its propagation through the medium along the first propagation direction and for a received second acoustic wave a second receive signal is generated after its propagation through the medium along the second propagation direction.

According to the invention it now is provided that for the determination of a runtime difference of the acoustic waves and/or an absolute runtime of an acoustic wave from a transmitter to a receiver a total of at least four receive signals—two first and two second receive signals—are utilized, which originate from at least two different transmit signals. These transmit signals substantially have the same fundamental frequency and a specified phase offset to each other. By using the identical—in one variant also the same—transmit signal, a first and a second acoustic wave thus is each generated in each propagation direction, so that for each propagation direction receive signals are present.

For example, a transmit signal is utilized to generate two acoustic waves propagating in the medium along the first and the second propagation direction at the same time or one after the other, wherein for an acoustic wave propagating along the first propagation direction—e.g. downstream of a flow direction of a flowing medium—a first receive signal is generated, and for an acoustic wave propagating along the second propagation direction—upstream—a second receive signal is generated. According to the invention, another, phase-shifted transmit signal of the same fundamental frequency then is utilized to generate two further acoustic waves propagating in the medium along the first and the second propagation direction, wherein here for an acoustic wave propagating along the first propagation direction—downstream—there is likewise generated a further first receive signal different therefrom, and for an acoustic wave propagating along the second propagation direction—upstream—a further second receive signal different therefrom is generated.

A transmit signal can be emitted by different transmitters spatially spaced from each other for generating the two acoustic waves. Alternatively, it is also conceivable in principle that a single transmitter seated between two receivers initially triggers two acoustic waves in direction of the two receivers with one transmit signal or with two identical transmit signals, and subsequently triggers two further acoustic waves in direction of the receivers with one transmit signal of the same fundamental frequency, which is phase-shifted with respect to the previously emitted transmit signal, or with two transmit signals phase-shifted with respect to the previously emitted transmit signal. It merely is essential that in each propagation direction a pair of receive signals is generated, which originate from two different, phase-shifted transmit signals of the same fundamental frequency.

Transmit signals of substantially the same fundamental frequency here are understood to be those transmit signals which with regard to their fundamental frequency maximally differ from each other by 1/1000 with respect to a center frequency.

The idea underlying the present invention is to quickly and with comparatively low measurement uncertainty due to little usage of hardware during signal processing determine a runtime difference and/or an absolute runtime from the total of four receive signals, which originate from two different transmit signals of the same fundamental frequency and a specified phase offset to each other, and thereupon determine physical and/or chemical properties of the medium. Due to the inventive use of two different transmit signals, an expensive differential signal generation or synchronization of the transmission and receive signals is not necessary in the present invention. Moreover, it is not necessary to provide an expensive digital signal processing, as in particular for a possible digitalization of receive signals or a possible digitalization of signals resulting therefrom the otherwise regularly advantageous Fourier transformation can be omitted.

Preferably, the four analog or digitized receive signals in the present case are directly included in a calculation, i.e. in particular as parameters are included in a calculation equation converted by a signal processing device, in order to calculate a runtime difference and/or an absolute runtime. Consequently, there is not carried out e.g. a simple averaging of runtime differences calculated already with a receive signal pair. In a respectively preferred design variant, each of the receive signals rather is directly included in a calculation rule for a runtime difference and/or a calculation rule for an absolute runtime, so that a calculation only can take place when all four receive signals are present.

For example, for the calculation of a runtime difference it is provided that receive signals for received acoustic waves, which were generated by different transmit signals, are multiplied by each other—preferably crosswise.

For example, depending on the design of a signal processing device used, a multiplication of analog receive signals can be provided, with subsequent calculation of a runtime difference from digitized signals, i.e. signals obtained by sampling. An alternative variant on the other hand would be to first provide a multiplication of already digitized receive signals for a calculation of a runtime difference.

Independent thereof, a formula of the following form is used for the determination of a runtime difference $\Delta t$ from receive signals $y_0^r(t)$, $y_1^r(t)$; $y_0^s(t)$ and $y_1^s(t)$:

$$\frac{Z(t)}{N(t)} = \left\{ \frac{y_0^s(t) \cdot y_1^r(t) - y_0^r(t) \cdot y_1^s(t)}{y_0^r(t) \cdot y_0^s(t) - y_1^r(t) \cdot y_1^s(t)} \right\} \qquad \text{[Equation 1]}$$

In Equation 1, the variables provided with an index "0" represent those signals which originate from a first transmit signal $x_0$, whereas the signals designated with an index "1" originate from a second, phase-shifted transmit signal $x_1$ of the same fundamental frequency. A superscript "r" furthermore designates those signals which originate from first acoustic waves received in a first propagation direction, e.g. downstream of flowing medium. The signals designated with a superscript "s" in turn originate from second acoustic waves received in a second, preferably opposite propagation direction, e.g. upstream.

In a preferred design variant a runtime difference $\Delta t$ then is determined directly with the values for a numerator $Z(t)$ and a denominator $N(t)$, according to the following formula:

$$\Delta t = \frac{\arctan\left\{\frac{Z(t)}{N(t)}\right\}}{4\pi f} \qquad \text{[Equation 2]}$$

Herein, f represents a fundamental frequency for both transmit signals.

With slightly different fundamental frequencies $f_0$ and $f_1$ of the different transmit signals $x_0$, $x_1$, this fundamental frequency f for example also can be determined from the arithmetic mean of the two fundamental frequencies $f_0$ and $f_1$:

$$f = \frac{f_0 + f_1}{2} \qquad \text{[Equation 2.1]}$$

Thus, the individual receive signals $y_0{}^r(t)$, $y_1{}^r(t)$; $y_0{}^s(t)$, $y_1{}^s(t)$ need not be converted into an analytical signal by expensive post-processing, but at least two different signals $x_0(t)$ and $x_1(t)$ with the same fundamental frequency f and a given phase offset, preferably of 90°, are provided already on the transmitter side and also as reference.

The used transmit signals preferably have the following shape:

$$x_0(t)=w(t)\cdot\sin(2\pi f\cdot t+\sigma)$$

$$x_1(t)=w(t)\cdot\cos(2\pi f\cdot t+\sigma) \quad \text{[Equations 3]}$$

Wherein $\varphi$ designates a freely selectable starting angle and w(t) represents a window function which shows the carrier signals of the transmit signals $x_0$ and $x_1$ preferably phase-shifted by 90° and hides the same again after a certain period. Such window function for example also can comprise a coding modulation sequence. A particularly large range for the evaluation of the phase and runtime differences to be calculated, which relates to the total duration of a transmit signal formed as transmit burst, here is obtained when choosing a Blackman-Nuttal window.

A transmit signal $x_0$, $x_1$ thus preferably each comprises a vibration impulse or pulse burst, wherein the envelopes to the individual vibration pulses of the phase-shifted transmit signals substantially are identical to each other. The receive signals obtained from the transmit signals for the acoustic waves at least partly propagated through the medium particularly easily can directly be converted to amplitude and phase signals as well as runtimes and runtime differences on a common time base—also shifted in a defined way, without additional references as required e.g. in an IQ modulation and without divisions by values close to 0, as will be shown in detail below.

In a determination of a (mean) flow velocity $v_m$ of a flowing medium, the determination of the phase or runtime difference for the different first and second acoustic waves is based on the different direction-dependent runtimes in the medium.

Use is made here of the fact that in different propagation directions, e.g. downstream and hence in flow direction on the one hand and upstream and hence against the flow direction on the other hand, different sound velocities depending on the flow velocity occur. Thus, a sound velocity in flow direction is $c^r=c_0+v_m$ and a sound velocity against the flow direction is $c^s=c_0-v_m$, wherein $c_0$ each is the sound velocity in the resting medium.

When transmitter and receiver now absolutely are away from each other by a distance $l_0$ and in the projection on the flow direction of the medium by a distance l, the corresponding sound runtimes are obtained along this path for the individual acoustic waves:

$$t^r = t_0 - \Delta t = \frac{l_0 c_0}{(c_0^2 - v_m^2)} - \frac{l v_m}{(c_0^2 - v_m^2)} \quad \text{[Equation 4.1]}$$

in flow direction or $$t^s = t_0 + \Delta t = \frac{l_0 c_0}{(c_0^2 - v_m^2)} - \frac{l v_m}{(c_0^2 - v_m^2)} \quad \text{[Equation 4.2]}$$

against the flow direction.

For a runtime difference $\Delta t$ of the first and second acoustic waves the following hence is obtained $$2\Delta t = t^s - t^r = \frac{2 l v_m}{(c_0^2 - v_m^2)} \approx 2 v_m \frac{1}{c_0^2} \quad \text{[Equation 5]}$$

The runtime difference $\Delta t$ thus is almost proportional to the mean flow velocity $v_m$.

The corresponding proportionality factor $1/(c_0)^2$ for example can be specified by the (one-time) determination of an absolute runtime of an acoustic wave from a transmitter to a receiver. For this purpose, a method according to the invention can be used for determining an absolute runtime. With a known distance between transmitter and receiver of a particular transmitter-receiver arrangement and a known sound velocity in a particular medium, whose flow velocity is to be measured and/or monitored, the proportionality factor also can firmly be set in the signal processing device.

Thus, by means of the two phase-shifted transmit signals $x_0$, $x_1$, the receive signals $$y_0{}^s(t)=x_0(t-(t_0+\Delta t)), \; y_1{}^s(t)=x_1(t-(t_0+\Delta t))$$

$$y_0{}^r(t)=x_0(t-(t_0-\Delta t)), \; y_1{}^r(t)=x_1(t-(t_0-\Delta t)) \quad \text{[Equation 6]}$$

are generated.

Sending all four transmit signals at the same time, i.e. sending a transmit signal $x_0$ in flow direction and against the flow direction, and sending a transmit signal $x_1$ in flow direction and against the flow direction, here is regarded as advantageous, in order to for example multiply the analog receive signals $y_0{}^r(t)$, $y_1{}^r(t)$; $y_0{}^s(t)$, $y_1{}^s(t)$ with each other in crosswise manner corresponding to Equation 1 and subsequently perform sampling with a small sampling rate for digitizing the resulting values Z(t) and N(t).

Alternatively, the individual transmit signals also can be sent one after the other and hence acoustic waves can be generated one after the other. The individual transmit signals thus are sequentially generated by the respective transmitter(s) and the receive signals also are sequentially generated at the receiver or at the receivers. Preferably, a high sampling rate is employed.

With four distinguishable receive signals, which originate from two phase-shifted transmit signals, not only a determination of a runtime difference, but also the determination of an absolute runtime is possible, as already explained above. Moreover, it would not be absolutely necessary either that the acoustic waves propagate through the medium along at least two first and second propagation directions different from each other. Even with identical propagation directions an absolute runtime would be determinable on the basis of the solution according to the invention by means of four distinguishable receive signals.

There is preferably employed an estimated starting value and a differential value calculated from the four receive signals. A differential value precisely calculated from the four receive signals is added to the (roughly) estimated starting value. What is important here is the definition of a robust runtime criterion, for example the location of the cross correlation maximum in the shift time range. In general, it is desirable that the measurement uncertainty at the estimated starting value for the runtime is smaller than half a period duration 1/f of the used carrier signal for the transmit signals (e.g. $x_0$ and $x_1$ corresponding to the above Equations 3).

A general calculation for an absolute runtime $t_0$ from a starting value $\hat{t}_0$ and a differential value $$t_0 = \hat{t}_0 - \Delta t' = \hat{t}_0 - \frac{\Delta \varphi'}{2\pi f} \qquad \text{[Equation 7]}$$

Δt' generally is required such that the following applies:

It was found to be advantageous, for example, when for the calculation of the differential value Δt' at least one of the following terms is utilized:

$$\alpha = \text{atan } 2(y_1^r(t+\hat{t}_0), y_0^r(t+\hat{t}_0)) - 2\pi \hat{f} \cdot (t + t_k)$$

$$\beta = \text{atan } 2(y_1^s(t+\hat{t}_0), y_0^s(t+\hat{t}_0)) - 2\pi \hat{f} \cdot (t + t_k) \qquad \text{[Equations 8]}$$

Herein, $\hat{f}$ is an estimated value for the center frequency of the receive signals $y_0^r$, $y_1^r$; $y_0^s$, $y_1^s$ and $t_k$ is a specified time constant with $t_k \geq 0$.

The function "a tan 2" represents an arc tangent function well known in programming and to be determined with less calculation effort, which for example can be defined via the following property:

$$\text{atan2}(y, x) = \begin{cases} \arctan\left(\frac{y}{x}\right) & x > 0 \\ \arctan\left(\frac{y}{x}\right) + \pi & x < 0, y \geq 0 \\ \arctan\left(\frac{y}{x}\right) - \pi & x < 0, y < 0 \\ +\frac{\pi}{2} & x = 0, y > 0 \\ -\frac{\pi}{2} & x = 0, y < 0 \\ NaN & x = y = 0 \end{cases} \qquad \text{[Equation 9]}$$

For example corresponding to the above Equations 7 and 8, a differential value Δt' and hence an absolute runtime $t_0$ then can be calculated comparatively easily by a signal processing device without Fourier transform by means of the following formula:

$$\Delta \varphi' = \frac{1}{2}(\alpha \bmod 2\pi + \beta \bmod 2\pi) - \pi \qquad \text{[Equation 10]}$$

An alternative possibility is represented by a formula as follows:

$$\Delta \varphi' = \qquad \text{[Equation 11]}$$

$$\frac{1}{2}\left\{ \begin{array}{l} \text{atan2}(-\sin\alpha, 1 - \cos\alpha) - \alpha\text{tan2}(\sin\alpha, 1 - \cos\beta) + \\ \text{atan2}(-\sin\beta, 1 - \cos\beta) - \text{atan2}(\sin\beta, 1 - \cos\beta) \end{array} \right\}$$

A further alternative is a calculation by the following method:

$$\Delta \varphi' = \gamma \cdot \pi - \arctan\left(\cot\frac{\alpha}{2}\right) - \arctan\left(\cot\frac{\beta}{2}\right) \qquad \text{[Equations 12]}$$

mit $\gamma = 0$, $$5 \cdot \text{sign}(\sin\alpha) \cdot (\text{sign}(1 - \cos\alpha) + \text{sign}(1 - \cos\beta) - 2)$$

In addition, a calculation rule of the following form also was found to be advantageous:

$$\Delta \varphi' = \frac{1}{2}(\alpha' \bmod 2\pi + (\beta' \bmod 2\pi) - \pi \qquad \text{[Equation 13.1]}$$

with $$\alpha' = \qquad \text{[Equation 13.2]}$$
$$\text{atan2}(y_0^r(t + \hat{t}_0), -y_1^r(t + \hat{t}_0)) - 2\pi \hat{f} \cdot (t + t_k) - \frac{\pi}{2}$$
$$\beta' = \text{atan2}(y_0^s(t + \hat{t}_0), -y_1^s(t + \hat{t}_0)) -$$
$$2\pi \hat{f} \cdot (t + t_k) - \frac{\pi}{2}$$

An error on estimation of the center frequency $\hat{f}$ can be corrected by approximating the runtimes of the signal groups observed by a straight line. The function value of this straight line at the estimated starting value $\hat{t}_0$ then is the best approximation for the absolute runtime $t_0$, namely largely independent of the center frequency $\hat{f}$ set up for calculation.

An adjustment (zero-point calibration) for example can be effected by setting the starting angle φ of the transmit signals $x_0$ and $x_1$ or by addition of the time constant $t_k$ to the time-proportional compensation term.

An estimation for the starting value $\hat{t}_0$ during the calculation of the absolute runtime $t_0$ likewise can be effected with reference to the four receive signals $y_0^r(t)$, $y_1^r(t)$; $y_0^s(t)$, $y_1^s(t)$ generated on receipt of the acoustic waves. For example, a starting value for the runtime calculation can be specified by means of at least one signal envelope $y_{huel}$, which is given by the following formula:

$$y_{juel} = \sqrt{y_0^2 + y_1^2} \qquad \text{[Equation 14.1]}$$

or more exactly $$y_{huel}^r = \sqrt{(y_0^r)^2 + (y_1^r)^2} \text{ or } y_{huel}^s = \sqrt{(y_0^s)^2 + (y_1^s)^2} \qquad \text{[Equations 14.2]}$$

Consequently, for example, a starting value $\hat{t}_0$ initially can be estimated by the signal envelope and subsequently an absolute runtime $t_0$ can be determined via a (subsequently calculated) differential value Δt'. With the absolute runtime $t_0$ for example the proportionality factor $1/(c_0)^2$ can be calculated and after a determination of a runtime difference Δt a flow velocity of the flowing medium can be determined.

In one design variant it can also be provided that when determining several values for runtime differences and/or for absolute runtimes of a plurality of acoustic waves averaging and/or integrating the determined runtime differences and/or runtimes is carried out, in order to minimize possible measurement uncertainties.

In a manner known per se, it is of course possible to determine a sound velocity, a concentration, a density and/or a temperature of the respective medium by means of the determined runtime difference and/or by means of the determined absolute runtime of the generated first and second acoustic waves, just like a filling level of the medium in an interior space, a thickness of a wall adjoining the medium and/or a distance of two wall portions adjoining the medium, as is also explained e.g. in WO 2008/034878 A2 in connection with surface acoustic waves.

Another aspect of the present invention is the provision of a device, which in particular is formed and provided for carrying out a method according to the invention.

Such device for determining physical and/or chemical properties of a medium includes at least the following:
  an acoustic waveguide which includes an interior space to be filled with the medium,
  at least two transmitters which each are formed and provided for the generation of acoustic waves in the waveguide by a transmit signal of the transmitter, so that a generated acoustic wave propagates along the waveguide and at least partly through the medium, at least two receivers which are spatially spaced from each other along the waveguide and each are formed and provided for the generation of a first or second receive signal for first or second acoustic waves reaching the respective receiver, wherein a first acoustic wave each propagates along a first propagation direction and for this purpose a first receive signal is generated at a receiver and a second acoustic wave each propagates along a second propagation direction identical to or different from the first propagation direction and for this purpose a second receive signal is generated at a receiver, and a signal processing device by means of which from the receive signals,
when the second propagation direction is different from the first propagation direction, a runtime difference between received first and second acoustic waves and/or,
when the second propagation direction is different from or identical to the first propagation direction, an absolute runtime of an acoustic wave from a transmitter to a receiver is determined, and which is formed and provided to determine physical and/or chemical properties of the medium with a determined runtime difference and/or a determined absolute runtime.

Analogous to the methods according to the invention the transmitters of the device furthermore are formed and provided to each generate first and second acoustic waves with two different transmit signals of the same fundamental frequency and specified phase offset to each other, so that in the first propagation direction two distinguishable first and in the second propagation direction two distinguishable second receive signals are generated by the receivers of the device. The signal processing device then is formed and provided to determine a runtime difference and/or an absolute runtime by the four generated receive signals, wherein preferably the aforementioned equations deposited in the signal processing device each are utilized for this purpose.

What was found to be particularly advantageous is the use of ultrasonic transducers as transmitter or receiver, which are formed and provided for the generation of surface acoustic waves in a waveguide of the device. Analogous to a device known from WO 2008/034878 A2 such device then among other things is characterized by an acoustic waveguide which comprises at least two opposite guide elements which define an interior space to be filled with a medium and which on filling the interior space with a medium each with one inner surface form a boundary surface with the medium. On the respective inner surface at least a part of the surface acoustic wave generated by a transmitter then is converted into volumetric sound waves of the medium and at least a part of the volumetric sound waves in turn is converted into surface acoustic waves of the waveguide, which then can be received at the respective receiver.

In such a device, especially, a method according to the invention can be realized particularly efficiently, as here the distinguishable four receive signals are formed for a comparatively very small balance space and with distinctly reduced expenditure for signal processing excellent results are achieved, which, as could be confirmed by corresponding simulations and experiments, have an extremely low measurement uncertainty. Thus, with distinctly reduced calculation effort, even a higher measurement accuracy possibly can be achieved in the determination of a flow velocity of a flowing medium.

In a possible design variant of a device according to the invention, the signal processing device includes means for the multiplication of analog receive signals and means for the subsequent calculation of a runtime difference from digitized signals, i.e. signals obtained by sampling. The means for the multiplication of analog receive signals for example comprise multipliers, adders and/or inverters. For digitizing, for example, at least one analog-to-digital converter of the device is used.

Alternatively, the signal processing device can include means for digitizing the receive signals and means for the subsequent multiplication of digitized receive signals for the calculation of a runtime difference. One design variant by way of example provides that the receive signals are supplied to an analog-to-digital converter via a multiplexer and only the digitized signals coming from the analog-to-digital converter are processed further e.g. corresponding to the above equations, in order to therefrom calculate a runtime difference $\Delta t$ and/or an absolute runtime $t_0$.

Furthermore, it can be provided in principle that the fundamental frequency of the two different, phase-shifted transmit signals just like their phase offset is variable and thus adjustable. Corresponding to the above Equation 3 it is preferred when the phase offset of the two transmit signals $(x_0, x_1)$ lies between 45° and 135° and for example in essence is 90° or $\pi/2$.

For the generation of the four acoustic waves by the two different transmit signals and the receipt of the associated four receive signals individual transmitters or receivers can of course be provided in the measuring device. It is preferred, however, when the device includes at least one transmitter-receiver unit which selectively is operable as transmitter or as receiver, so that via a transmitter-receiver unit in a transmitter mode both a transmit signal can be generated for an acoustic wave in the one propagation direction, and in the receiver mode an acoustic wave which has propagated in the other propagation direction towards the transmitter-receiver unit, thereby can be received and a corresponding receive signal can be generated.

In a possible development, a transmitter-receiver unit is an ultrasonic transducer which preferably also is suitable for a pulse-echo technique, in order to generate transmit signals and receive acoustic waves on the basis of which the ultrasonic transducer generates receive signals.

BRIEF DESCRIPTION OF THE DRAWINGS

In addition, further advantages and features of the present invention will become apparent from the following description of exemplary embodiments with reference to the Figures.

FIG. 3 schematically shows a further design variant of a device according to the invention, in which a signal processing means includes a demultiplexer and a multiplexer as well as an analog-to-digital converter, in order to digitize generated receive signals before their further processing and in particular their multiplication and addition.

DETAILED DESCRIPTION

Figure 4:
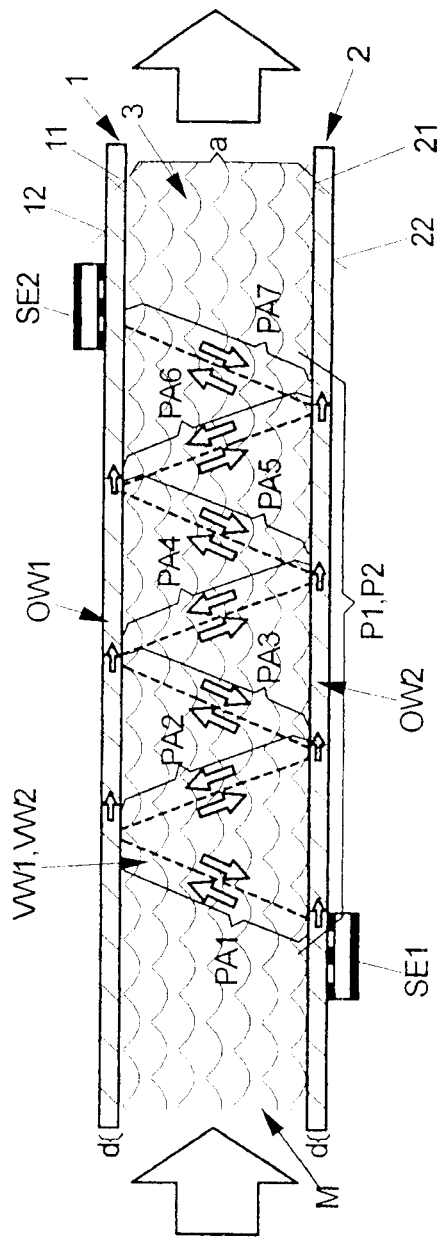
FIG. 4 shows a device for determining a flow velocity of a flowing medium by means of surface acoustic waves, which is known from the prior art.

In the sectional view of FIG. 4, a (measuring) device already known per se is partly shown, which is formed and provided for the determination of physical and/or chemical properties of a medium M, in particular for the determination or measurement of a flow velocity of the flowing medium M. An acoustic waveguide with two substrates 1, 2 as guide elements of the waveguide is part of the measuring device, wherein the medium M flows through the waveguide. The substrates 1, 2, which oppose each other and whose (inner) surfaces 11, 21 pointing towards each other extend parallel to each other along a main direction of extension of the waveguide, are made of a non-piezoelectric material.

These substrates 1, 2 oppose each other at a distance a and in the present case are bordered by two plates opposing each other at this distance a or by wall portions of a tube opposing each other, which form a (channel-shaped) interior space 3 of the waveguide. In the interior space 3 the medium M to be measured, which is schematically represented by undulating lines, is filled in, wherein the medium M can flow through the interior space 3. The flow direction of the liquid or flowable medium M through the interior space 3 in principle is arbitrary. In the present case, the flow is from an inlet opening to an outlet opening along the main direction of extension of the waveguide and parallel to the inner surfaces 11, 21. In FIG. 4, the flow direction is indicated by arrows at the outlet and inlet opening, respectively.

To the two (first and second) substrates 1 and 2 of the waveguide of the device a (first) transmitter-receiver unit SE1 or a (second) transmitter-receiver unit SE2 is associated. Each transmitter-receiver unit SE1, SE2 is operable in at least two different operating modes on the one hand as transmitter and on the other hand as receiver, in order to induce or receive acoustic waves. Thus, for example the first transmitter-receiver unit SE1 of the second substrate 2 (initially) can be operated as transmitter, while the second transmitter-receiver unit SE2 of the first substrate 1 is operated as receiver.

The transmitter-receiver units SE1, SE2 each are arranged on an outer surface 22 or 12 of the respective substrate 2 or 1, which each opposes an inner surface 21 or 11 facing the interior space 5 with the medium M. The two transmitter-receiver units SE1, SE2 preferably are piezoelectric transducers with interdigital electrodes. Preferably, the attachment of a transmitter-receiver unit SE1, SE2 to the respective substrate 2, 1 is effected by gluing, so that the same is to be mounted quickly and easily. Alternatively, other types of attachment can also be provided.

In the present case, the first transmitter-receiver unit SE1 of FIG. 4 is located in the region of a first end of the waveguide, while the second transmitter-receiver unit SE2 is arranged in the region of another, second end of the waveguide and in the illustrated cross-sectional view the waveguide extends between these two ends along a main direction of extension.

Via a transmitter-receiver unit, e.g. SE1, operating as transmitter, surface acoustic waves OW2 are generated in the substrate 2 by means of a specified, preferably pulse-like transmit signal. At the boundary surface of the inner surface 21, a part of the energy of these generated surface acoustic waves OW2 is coupled into the medium M as volumetric sound wave VW1. The propagation of a volumetric sound wave VW1 and the propagation direction of the volumetric sound wave VW1 are schematically represented in FIG. 4 by a broken line and by an arrow beside this broken line. By two oppositely directed arrows beside the broken lines it is expressed that volumetric sound waves propagate along path portions PA1 to PA7 represented by the broken lines in one operating mode of the device in the one direction and in another operating mode of the device in the other direction.

The two substrates 1, 2, which form the inner surfaces 11, 21, preferably consist of a non-piezoelectric material and have a thickness d which is defined as the distance of the inner surfaces 11, 21 of the respectively associated outer surfaces 12, 22. In the present case, the thickness d is equal to or smaller than the wavelength of the respectively generated surface acoustic waves. As a result, surface acoustic waves which propagate within the substrates 1, 2 can have wave properties such that they propagate both along the inner surfaces 11, 21 and along the outer surfaces 12, 22 of the plate-shaped substrates 1, 2. Thus, Lamb waves or waves in the transition region of Lamb waves and Rayleigh waves are induced. In dependence on the thickness d of the plates of the substrates 1, 2 surface acoustic waves substantially in the form of Lamb waves (d smaller than the wavelength of the surface acoustic waves) or in the form of waves from the transition region between Lamb waves and Rayleigh waves (d equal to the wavelength of the surface acoustic waves) will be present. In each case, the surface acoustic waves propagate along both surfaces 11, 12 and 21, 22 of the substrates 1 and 2, respectively.

As is illustrated in FIG. 4, e.g. the surface acoustic waves OW2 hence extend proceeding from the transmitter-receiver unit SE1 operating as transmitter along the direction of extension of the second substrate 2 and in particular along the inner surface 21 of this substrate 2. A part of the sound wave energy of the surface acoustic waves OW2 running along the inner surface 21 of the substrate 2 is coupled into the medium M present within the interior space 3, so that volumetric sound waves VW1 are generated within the medium M. A propagation direction of these volumetric sound waves VW1 coupled in is inclined relative to the normal on the flat surface 21 by a characteristic angle A, which is not indicated.

The volumetric sound waves VW1 each propagate in the medium M along a path P1. This path can be divided into various portions PA1, PA2, PA3, PA4, PA5, PA6, PA7 represented by broken lines. Each of these path portions extends between the one (second) substrate 2 and the other (first) substrate 1. As soon as the volumetric sound wave VW1 has arrived at an interaction point on the inner surface 11 of the opposite substrate 1, a part of its energy is coupled into the substrate 1, so that surface acoustic waves OW1, for example in the form of Lamb waves or surface waves in the transition region of Lamb waves and Rayleigh waves, herein are generated, which propagate along this substrate 1.

Furthermore, at each point in time at which the volumetric sound wave VW1 arrives at the inner surface 11 or 21 of one of the substrates 1, 2, an interaction of this sound wave with the corresponding substrate 1, 2 occurs. In general, an exchange of acoustic energy occurs between the substrate 1, 2, in particular the surface wave OW1, OW2 of the respective substrate 1, 2, and the volumetric sound wave VW1. The volumetric sound wave VW1 is at least partly reflected and changes its propagation direction. When the interaction consists in coupling in energy from the volumetric sound wave VW1 into the respective surface wave OW1, the amplitude of the surface wave OW1 is increased by such coupling in and the amplitude of the volumetric sound wave VW1 decreases. Alternatively, in dependence on the properties of the substrate and of the medium M as well as of the wave, coupling in of energy of the surface wave OW1 into the volumetric sound wave VW1 also can be effected.

As a result of the interaction of the volumetric sound wave VW1 with the substrates 1, 2 along its path P1 several interaction points thus are defined. At these interaction points the volumetric sound wave VW1 each interacts with a substrate 1, 2 and the surface waves OW1, OW2 occurring in the substrate 1, 2. In general, (first) wave trains comprising volumetric sound waves VW1 thus propagate on a substantially zigzag-shaped propagation path P1 in the medium between the first transmitter-receiver unit SE1 and the second transmitter-receiver unit SE2 along the main direction of extension of the waveguide. Due to the interaction of the volumetric sound wave VW1 with the first substrate 1 opposite the second substrate 2 on its inner surface 11, the surface waves OW1 are induced, which propagate on the substrate 1 and finally can be received at the transmitter-receiver unit SE2 operating as receiver. Between the interaction points of the second substrate 2, i.e. those points at which the volumetric sound waves VW1 interact with the second substrate 2, the surface waves OW1 propagate without amplification, but at the following interaction point (possibly) experience a further amplification. By measuring the wave trains arriving at the receiver E, in particular the surface waves OW1 which were induced by interaction with the volumetric sound wave VW1, the runtime of wave trains between the first and the second transmitter-receiver unit SE1, SE2 can be determined.

From surface acoustic waves OW1 (or groups of surface waves OW1), which one after the other arrive at the transmitter-receiver unit SE2 operating as receiver, the sound velocity within the medium M thus can be inferred, in particular when the runtime of the wave trains between the transmitter-receiver units SE1, SE2 is determined. Since the measured runtimes of the surface acoustic waves OW1 coupled in at the respective interaction points via the volumetric sound wave VW1 are influenced by the properties of the medium M, physical and/or chemical properties of the medium M to be measured thus can be determined by a (non-illustrated) electronic evaluation unit to which the signals of a transmitter-receiver unit SE2 are forwarded. From an acoustic wave received at the transmitter-receiver unit SE2 or SE1, which as volumetric sound wave VW1 (or VW2) has at least partly propagated through the medium M from the other transmitter-receiver unit SE1, SE2 to this transmitter-receiver unit SE2, SE1, a receive signal each is generated.

It should be noted that at a receiver or a transmitter-receiver unit SE2 operated in the receiver mode usually surface waves OW1 exclusively are received, wherein these surface waves OW1 originate from the volumetric sound wave VW1 impinging on the first substrate 1. The determined temporal differences between the receipt of one or more surface wave(s) correspondingly also is utilized as a basis for the determination of the flow velocity, as will yet be explained in detail below.

The device of FIG. 4 for this purpose can be operated via a multiplexer in two different operating modes, i.e. the second transmitter-receiver unit SE2 previously operated in a receiver mode also is operated in a transmitter mode and the first transmitter-receiver unit SE1 previously operated in the transmitter mode is operated in the receiver mode. By the second transmitter-receiver unit SE2 operated in the transmitter mode an surface acoustic wave OW1 now is induced in the first substrate 1. As before, at least a part of the energy of this surface acoustic wave OW1 is converted into energy of an acoustic volumetric sound wave VW2 propagating in the medium 2, which now propagates on a propagation path P2 from the second transmitter-receiver unit SE2 to the first transmitter-receiver unit SE1 through the medium M. The surface wave OW1 of a second acoustic wave, which is induced by the second transmitter-receiver unit SE2, thus proceeds from this transmitter-receiver unit SE2, so that the volumetric sound wave VW2 induced thereby extends substantially opposite to the preceding volumetric sound wave VW1 and on zigzag line through the medium M in direction of the first transmitter-receiver unit SE1.

By switching between transmitter and receiver mode of the transmitter-receiver units SE1, SE2, the running direction of the volumetric sound waves VW1, VW2 within the medium M hence is reversed along the main propagation direction of the waveguide. The result is that depending on the operating mode (first or second) wave trains or first or second acoustic waves on the one hand propagate between the two transmitter-receiver units SE1 and SE2 such that they have path portions PA1 to PA7 extending in the medium, along which they have a propagation velocity vector with a vectorial propagation velocity component in direction of the flow of the medium M (first wave trains), and on the other hand propagate such that they have path portions PA7 to PA1 extending in the medium, along which they have a propagation velocity vector with a vectorial propagation velocity component in the direction opposite to the flow of the medium M (second wave trains). Consequently, the runtimes for surface waves of a second wave train received at the first transmitter-receiver unit SE1 differ from the runtimes for surface waves of a first wave train received at the second transmitter-receiver unit SE2 due to the flow of the medium M. By measuring the (absolute) runtimes of the two wave trains and/or by determining a difference of the runtimes of the opposite wave trains, it hence is possible in principle to determine the flow velocity of the medium M. Furthermore, via the propagation of the wave trains along the wave guide, information on the density or the concentration of substances in the medium M can be derived.

To infer a runtime difference or even the absolute runtime of an acoustic wave between the transmitter-receiver units SE1, SE2 with reference to signals received for arriving acoustic waves (receive signals) by no means is trivial, however, and possibly requires an enormous calculation effort. Moreover, this also applies for other measuring devices in which physical and/or chemical properties of a medium are determined by means of acoustic waves.

This is where a method according to the invention now comes into play, which among other things provides the sending of two phase-shifted transmit signals for generating acoustic waves and with which it is possible to make the evaluation of received signals more efficient in particular in a device with a waveguide according to FIG. 4 and among other things to considerably facilitate the determination of a runtime difference of acoustic waves propagating along different directions with reference to signals received.

According to FIG. 4, a measuring device known from the prior art is developed such that with two different transmit signals of the same fundamental frequency and a specified phase offset to each other transmitters of the device each generate first and second acoustic waves along the different propagation directions, preferably in flow direction and against the flow direction, so that in each propagation direction two different receive signals $y_0^r$, $y_1^r$ and $y_0^s$, $y_1^s$ each are generated by the receivers of the device. In addition, a signal processing device, e.g. $SV_A$ or $SV_B$, is provided, by means of which a runtime difference $\Delta t$ and/or an absolute runtime $t_0$ is determined by the four generated receive signals $y_0^r$, $y_1^r$, $y_0^s$ and $y_1^s$.

Figure 1A:
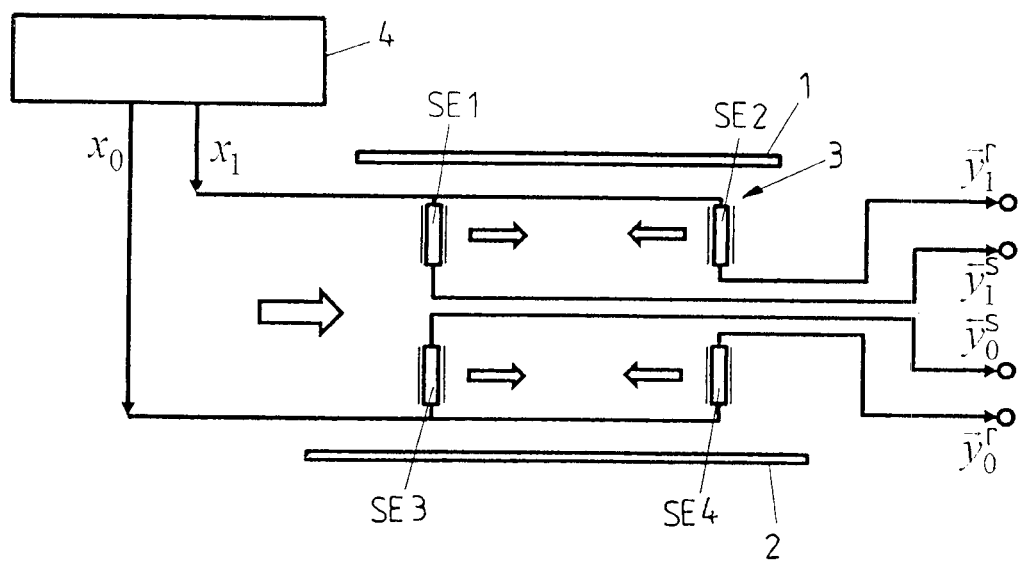
FIG. 1A schematically shows a design variant of a device according to the invention, which is formed and provided for carrying out the methods according to the invention and in particular for determining a flow velocity of a flowing medium.

In one design variant of FIG. 1A a signal generator 4 coupled with several transmitter-receiver units SE1, SE2, SE3 and SE4 or integrated therein is provided, so that via two transmitter-receiver units SE1 and SE2 as well as SE3 and SE4 spatially spaced from each other along the longitudinal extension of the waveguide a transmit signal $x_1$ or a phase-shifted transmit signal $x_0$ of the same fundamental frequency can each be utilized for generating a (surface) acoustic wave.

Corresponding to the above-mentioned Equation 3, the individual transmit signals $x_0$, $x_1$ preferably have the following form:

$$x_0(t) = -w(t) \cdot \sin(2\pi f \cdot t + \varphi)$$

$$x_1(t) = w(t) \cdot \cos(2\pi f \cdot t + \varphi)$$

The individual transmitter-receiver units SE1 to SE4 here also each are formed such that they both can generate acoustic waves and receive acoustic waves. For example, a transmitter-receiver unit SE1 generates an acoustic wave propagating in flow direction (first propagation direction), which is received at the downstream transmitter-receiver unit SE2 and here generates a receive signal $y_1^r$. This transmitter-receiver unit SE2 in turn generates a second acoustic wave propagating in upstream direction (in the second, opposite propagation direction), which is received at the upstream transmitter-receiver unit SE1 and leads to the generation of a further receive signal $y_1^s$. Both receive signals $y_1^r$ and $y_1^s$ originate from a transmit signal $x_1$.

Via the arrangement of second transmitter-receiver units SE3-SE4, receive signals $y_0^s$ and $y_0^r$ likewise are generated with transmit signals $x_0$.

Figure 1B:
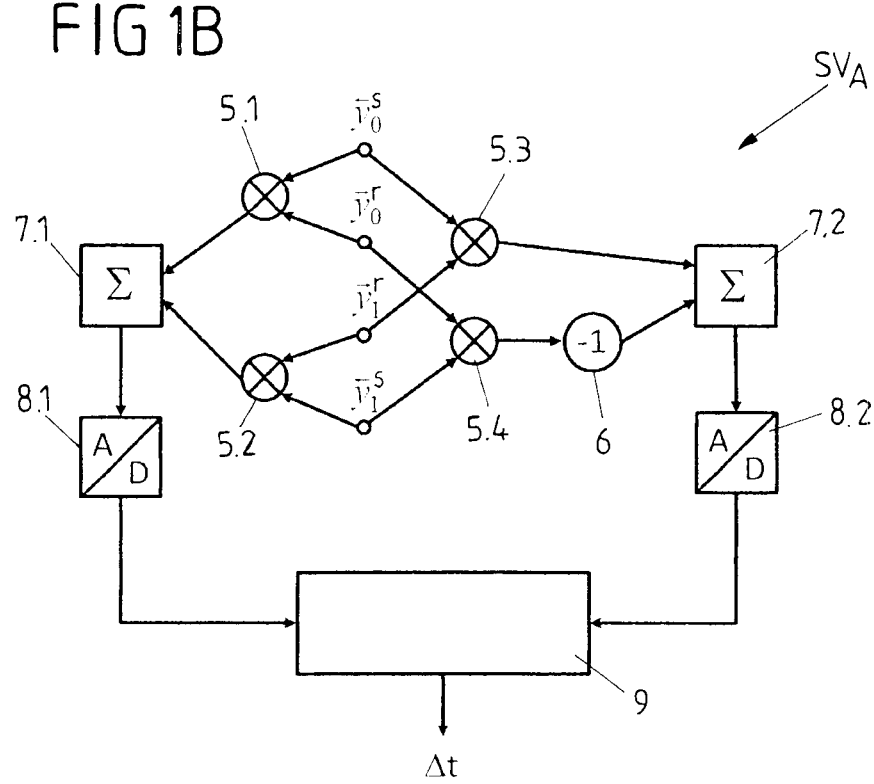
FIG. 1B schematically shows a signal processing device of the device of FIG. 1A, by means of which analog receive signals in particular are multiplied by each other and added, before they are digitized and processed further, in order to calculate a runtime difference.

Via a signal processing device $SV_A$ corresponding to FIG. 1B, the individual analog receive signals $y_0^r$, $y_1^r$; $y_0^s$, $y_1^s$ are processed. Corresponding to the above Equation 6, the following applies for the individual receive signals:

$$y_0^s(t) = x_0(t - (t_0 + \Delta t)), y_1^s(t) = x_1(t - (t_0 + \Delta t))$$

$$y_0^r(t) = x_0(t - (t_0 - \Delta t)), y_1^r(t) = x_1(t - (t_0 - \Delta t))$$

By the type of signal processing device $SV_A$ as shown in FIG. 1B, which here comprises a total of four multipliers 5.1, 5.2, 5.3 and 5.4 as well as two adders 7.1 and 7.2 and two analog-to-digital converters 8.1 and 8.2, the analog receive signals $y_0^r$, $y_1^r$; $y_0^s$, $y_1^s$ are processed corresponding to the above Equation 1 to obtain enveloping signals Z(t) and N(t) and are digitized.

Via a calculation unit, here represented as signal processing means 9, values for a runtime difference $\Delta t$ between the acoustic waves propagating in downstream and upstream direction then are obtained from these digitized enveloping signals Z(t) and N(t) corresponding to Equation 2.

With a known distance $l_0$ between the individual transmitter-receiver units SE1 and SE2 as well as SE3 and SE4 and with a known sound velocity $c_0$ in the medium M, which is present in the interior space 3, a (mean) flow velocity of the medium M in turn can be inferred corresponding to the above Equations 4.1, 4.2 and 5.

In addition, with a device according to FIG. 1A it is of course also possible to obtain a proportionality factor ($1/(c_0)^2$) from an absolute runtime $t_0$ with reference to the four receive signals $y_0^r$, $y_1^r$; $y_0^s$, $y_1^s$ in that the signal processing device $SV_A$ for example includes means for converting Equation 7 explained above.

The determination of the runtime difference $\Delta t$ with a signal processing device $SV_A$ captivates with its simplicity, as by using simple circuitry components it permits to reliably infer the runtime difference of the acoustic waves in the different propagation directions, in particular without having to utilize a Fourier transformation during signal processing.

Figure 2A:
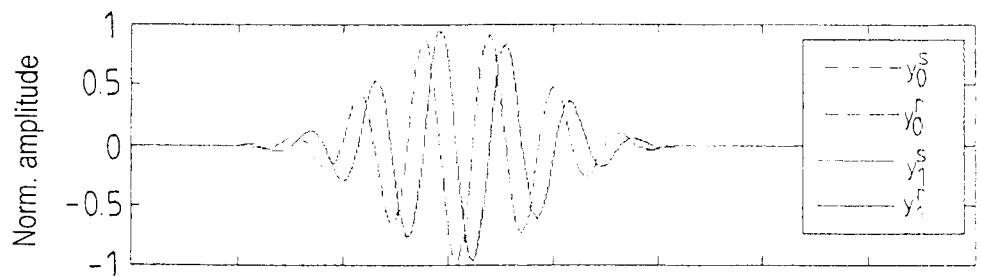
FIG. 2A shows a diagram which illustrates the standardized amplitude curve of the receive signals in a device according to FIGS. 1A and 1B, when the same utilizes transmit signals corresponding to the above Equation 3 for the generation of acoustic waves.
Figure 2B:
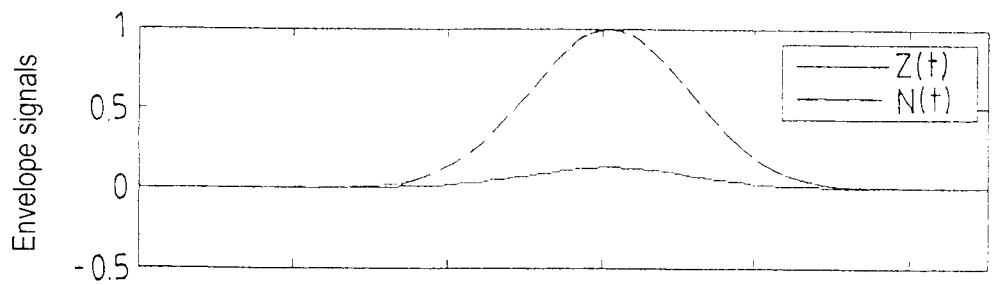
FIG. 2B shows a diagram which illustrates the course of signals Z(t) and N(t) obtained from the receive signals of FIG. 2A corresponding to the above Equation 1.
Figure 2C:
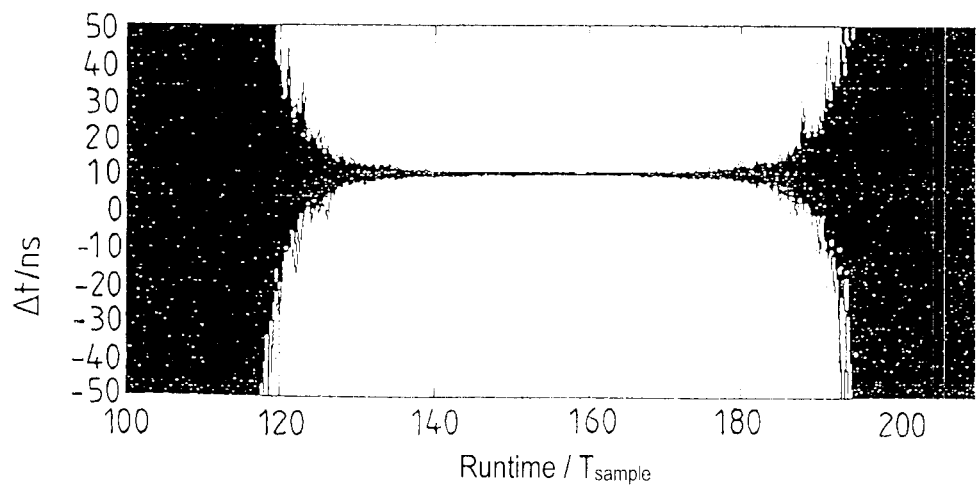
FIG. 2C shows superimposed runtime differences from the signals of FIGS. 2A and 2B in 1000 simulated, differently noisy and shifted signal courses, wherein the actual runtime difference was 10 ns.

With reference to FIGS. 2A, 2B and 2C signal courses determined by simulations will be represented and in particular with reference to FIG. 2C the achieved measurement accuracy in the determination of a runtime difference $\Delta t$ will be illustrated.

FIG. 2A shows a standardized amplitude curve for the individual receive signals $y_0^r$, $y_1^r$; $y_0^s$, $y_1^s$. In FIG. 2B, the resulting signals Z(t) and N(t) (see Equation 1) in turn are plotted.

FIG. 2C now shows the derived and determined runtime differences $\Delta t$ in dependence on the sampling time $T_{sample}$ when sampling via the signal processing device $SV_A$. A total of 1000 different noisy and shifted signal courses were simulated, and the results are superimposed in FIG. 2C. It can be seen that with the realization of the method according to the invention the specified runtime difference value of 10 ns always is hit well in the signal focus, especially with the comparatively simple and hence inexpensive construction of the signal processing device $SV_A$.

While in the design variant according to FIG. 1A sending all four transmit signals at the same time or actuating four different transmitter-receiver units SE1 to SE4 in the form of ultrasonic transducers at the same time—preferably embedded in a single ultrasonic sensor of a (measuring) device according to the invention—is provided with two different transmit signals $x_0$ and $x_1$, sending of transmit signals $x_0$ and $x_1$ offset in time can of course also be provided. A possible design variant is schematically shown in FIG. 3.

A design variant of a measuring device according to the invention in particular for determining a (mean) flow velocity $y_m$ of a medium M present in the interior space 3 here is provided with an alternative signal processing device $SV_B$, which among other things comprises a multiplexer 40 and a demultiplexer 90. The signal generator 4 specifying the transmit signals $x_0$ and $x_1$, which here again is part of an arrangement with two transmitter-receiver units SE1 and SE2, is coupled with the multiplexer 40, in order to supply the individual transmit signals $x_0$ and $x_1$ to the transmitter-receiver units SE1 and SE2 with a time offset. Thus, each transmitter-receiver unit SE1 or SE2 is able to generate first or second acoustic waves in flow direction or against the flow direction by using different transmit signals $x_0$, $x_1$.

The receive signals $y_0^r$, $y_1^r$; $y_0^s$, $y_1^s$ then are supplied by the transmitter-receiver units SE1 and SE2 to the demultiplexer 90 one after the other in analog form and then are digitized via a downstream analog-to-digital converter 8. The digitized signals then are utilized here for the calculation of the runtime difference $\Delta t$ and/or the absolute runtime $t_0$ in the signal processing means 9, e.g. corresponding to the above Equations 7, 8 and 10.

With the devices according to the invention and with the method according to the invention to be carried out thereby, the time-dependent courses of amount and phase of transmitted or reflected ultrasonic signals and the signal runtimes or runtime differences derived therefrom can be determined in a particularly simple and efficient way. The use of hardware also can be limited to a minimum. The realized method for determining a runtime difference $\Delta t$ and/or a method for determining an absolute runtime $t_0$ is extremely robust and involves a low measurement uncertainty, when, as shown, four different receive signals $y_0^r$, $y_1^r$; $y_0^s$, $y_1^s$ are employed, which originate from two different transmit signals $x_0$, $x_1$ with the same fundamental frequency f and with a specified phase offset to each other.

In addition, it should also be noted that the frequency sequence or the frequency response of the transmit signals $x_0$, $x_1$ preferably is identical for each measurement carried out, but the fundamental frequency f can be varied for different measurements, i.e. in particular for different measurement arrangements and/or media.

Moreover, pulse-like transmit signals are preferred in principle, which lead to pulse-like receive signals $y_0^r(t)$, $y_1^r(t)$; $y_0^s(t)$, $y_1^s(t)$ corresponding to FIG. 2A. In principle, however, a continuous excitation of acoustic waves at the respective transmitters or transmitter-receiver units SE1 to SE4 also would be conceivable.

In addition, it is quite obvious that with the illustrated devices and the methods realized therewith not only a (mean) flow velocity $v_m$ of a flowing medium M can be determined, but also—alternatively or in addition—a concentration, thickness, distance, temperature and/or filling level measurement can be carried out, as it is widely known already in comparable devices which employ acoustic waves, in particular ultrasonic waves. The same applies for the determination of time-dependent courses of the instantaneous amplitude or instantaneous phase of the acoustic waves received and of values for density and viscosity of the medium M derived therefrom.

LIST OF REFERENCE NUMERALS 1 (first) substrate
11 inner surface
12 outer surface
2 (second) substrate
21 inner surface
22 outer surface
3 interior space
4 signal generator
40 multiplexer
5.1-5.4 multiplier
6 inverter
7.1, 7.2 adder
8 analog-to-digital converter (A/D-converter)
8.1, 8.2 analog-to-digital converter (A/D-converter)
9 signal processing means
90 demultiplexer
a distance
d thickness
f fundamental frequency
M medium
OW1, OW2 surface acoustic wave
P1, P2 path
PA1-PA7 path portion
SE1, SE2, SE3, SE4 transmitter-receiver unit
$SV_A$, $SV_B$ signal processing device
$t_0$ runtime
$v_m$ mean flow velocity
VW1, VW2 volumetric sound wave
w window function
x transmit signal
$y^r$ first receive signal (downstream)
$y^s$ second receive signal (upstream)
$\varphi$ starting angle
$\Delta t$ runtime difference

The invention claimed is:

1. A method for determining physical and/or chemical properties of a medium on the basis of two first and two second acoustic waves, which each have at least partly propagated through the medium from at least one transmitter to at least one receiver, wherein:
the two first and two second acoustic waves each are generated by a transmit signal $x_0$, $x_1$,
the two first acoustic waves propagate through the medium along a first propagation direction and the two second acoustic waves propagate through the medium along a second propagation direction different from the first propagation direction,
for a received first acoustic wave a first receive signal $y_0^r$, $y_1^r$ is generated after its propagation through the medium along the first propagation direction and for a received second acoustic wave a second receive signal $y_0^s$, $y_1^s$ is generated after its propagation through the medium along the second propagation direction,
from the receive signals $y_0^r$, $y_1^r$; $y_0^s$, $y_1^s$ a runtime difference $\Delta t$ of the acoustic waves is determined and by means of a determined runtime difference $\Delta t$ physical and/or chemical properties of the medium are determined,
at least two different transmit signals $x_0$, $x_1$ of substantially the same fundamental frequency f are used, which have a specified phase offset to each other and by which, in each case, first and second acoustic waves each are generated, so that for each propagation direction, and based on the two transmit signals $x_0$, $x_1$, four receive signals $y_0^r$, $y_1^r$; $y_0^s$, $y_1^s$ are generated, which originate from different transmit signals $x_0$, $x_1$, and
a runtime difference $\Delta t$ of the acoustic waves propagating along the two different propagation directions is determined by the four receive signals $y_0^r$, $y_1^r$; $y_0^s$, $y_1^s$ of which two receive signals $y_0^r$, $y_0^s$ result from first and second acoustic waves generated by a first transmit signal $x_0$ of the two different transmit signals $x_0$, $x_1$ and two receive signals $y_1^r$, $y_1^s$ result from first and second acoustic waves generated by a second transmit signal $x_1$ of the two different transmit signals $x_0$, $x_1$.

2. The method according to claim 1, wherein the four receive signals $y_0^r$, $y_1^r$; $y_0^s$, $y_1^s$ are directly included in a calculation, in order to calculate a runtime difference $\Delta t$ and only when all four receive signals $y_0^r$, $y_1^r$; $y_0^s$, $y_1^s$ are present, a runtime difference $\Delta t$ is calculated.

3. The method according to claim 1, wherein for the determination of a runtime difference $\Delta t$ receive signals $y_0^r$, $y_1^r$; $y_0^s$, $y_1^s$ for acoustic waves are multiplied by each other, which were generated by different transmit signals $x_0$, $x_1$.

4. The method according to claim 3, wherein a multiplication of analog receive signals $y_0^r$, $y_1^r$; $y_0^s$, $y_1^s$ is provided, with subsequent calculation of a runtime difference ($\Delta t$) from digitized signals, or that for a calculation of a runtime difference $\Delta t$ a multiplication of digitized receive signals $y_0^r$, $y_1^r$; $y_0^s$, $y_1^s$ is provided.

5. The method according to claim 1, wherein for the determination of a runtime difference ($\Delta t$) a formula of the following form is used:

$$\frac{Z(t)}{N(t)} = \left\{ \frac{y_0^s(t) \cdot y_1^r(t) - y_0^r(t) \cdot y_1^s(t)}{y_0^r(t) \cdot y_0^s(t) - y_1^r(t) \cdot y_1^s(t)} \right\},$$

wherein t is the time, and $y_0^s$ is the first receive signal for the acoustic wave generated by a first transmit signal $x_0$, $y_1^s$ is the first receive signal for the acoustic wave generated by a second transmit signal $x_1$, $y_0^r$ is the second receive signal for the acoustic wave generated by a first transmit signal $x_0$ in the other propagation direction, and $y_1^r$ is the second receive signal for the acoustic wave generated by a second transmit signal $x_1$ in the other propagation direction.

6. The method according to claim 5, wherein a runtime difference $\Delta t$ is determined by the following formula:

$$\Delta t = \frac{\arctan\left\{\frac{Z(t)}{N(t)}\right\}}{4\pi f}$$

wherein f herein is a fundamental frequency for both transmit signals $x_0$, $x_1$.

7. The method according to claim 6, wherein the two different transmit signals $x_0$, $x_1$ have fundamental frequencies $f_0$, $f_1$ slightly differing from each other, and a fundamental frequency f for the determination of the runtime difference $\Delta t$ is determined from the arithmetic mean of the two fundamental frequencies $f_0$, $f_1$.

8. The method according to claim 1, wherein the transmit signals $x_0$, $x_1$ each comprise a vibration impulse and envelopes to the individual vibration impulses of the phase-shifted transmit signals $x_0$, $x_1$ substantially are identical to each other.

9. The method according to claim 1, wherein at the same time or one after the other acoustic waves are generated by the transmit signals $x_0$, $x_1$.

10. The method according to claim 1, wherein by means of the runtime difference $\Delta t$ a flow velocity $v_m$ of a flowing medium M is determined and the acoustic waves are generated by the transmit signals $x_0$, $x_1$ such that first acoustic waves propagate through the medium M along a first propagation direction in flow direction of the medium M and second acoustic waves propagate through the medium M along a second propagation direction against the flow direction of the medium M.

11. The method according to claim 10, wherein a flow velocity is calculated by the runtime difference $\Delta t$ and a known proportionality factor.

12. A method for determining physical and/or chemical properties of a medium on the basis of at least two first and two second acoustic wave, which each have at least partly propagated through the medium from at least one transmitter to at least one receiver, wherein:

the two first and two second acoustic waves each are generated by a transmit signal $x_0$, $x_1$, the two first acoustic waves propagate through the medium along a first propagation direction and the two second acoustic waves propagate through the medium along a second propagation direction identical to or different from the first propagation direction, for a received first acoustic wave, a first receive signal $y_0^r$, $y_1^r$ is generated after its propagation through the medium along the first propagation direction and, for a received second acoustic way, a second receive signal $y_0^s$, $y_1^s$ is generated after its propagation through the medium along the second propagation direction, an absolute runtime $t_0$ of an acoustic wave from a transmitter to a receiver is determined from the receive signals $y_0^r$, $y_1^r$, $y_0^s$, $y_1^s$ and by means of a determined absolute runtime $t_0$ physical and/or chemical properties of the medium are determined, at least two different transmit signals $x_0$, $x_1$ of substantially the same fundamental frequency f are used, which have a specified phase offset to each other and with which a first and a second acoustic wave each is generated, so that for the first and second propagation directions, and based on the two transmit signals $x_0$, $x_1$, four receive signals $y_0^r$, $y_1^r$; $y_0^s$, $y_1^s$ are generated, which originate from different transmit signals $x_0$, $x_1$, and an absolute runtime $t_0$ of an acoustic wave between a transmitter and a receiver is determined by the four receive signals $y_0^r$, $y_1^r$; $y_0^s$, $y_1^s$ of which two receive signals $y_0^r$, $y_0^s$ result from first and second acoustic waves generated by a first transmit signal $x_0$ of the two different transmit signals $x_0$, $x_1$ and two receive signals $y_1^r$, $y_1^s$ result from first and second acoustic waves generated by a second transmit signal $x_1$ of the two different transmit signals $x_0$, $x_1$.

13. The method according to claim 12, wherein an absolute runtime $t_0$ is determined from an estimated starting value $\hat{t}_0$ and a differential value $\Delta t'$ calculated from the four receive signals $y_0^r$, $y_1^r$; $y_0^s$, $y_1^s$.

14. The method according to claim 13, wherein for the calculation of the differential value $\Delta t'$ at least one of the following terms is utilized:

$$\alpha = \operatorname{atan} 2(y_1^r(t+\hat{t}_0), y_0^r(t+\hat{t}_0)) - 2\pi \hat{f} \cdot (t+t_k)$$

$$\beta = \operatorname{atan} 2(y_1^s(t+\hat{t}_0), y_0^s(t+\hat{t}_0)) - 2\pi \hat{f} \cdot (t+t_k)$$

wherein $\hat{f}$ herein is an estimated value for the center frequency of the receive signals $y_0^r$, $y_1^r$; $y_0^s$, $y_1^s$ and $t_k$ is a specified time constant with $t_k \geq 0$, and $y_0^s$ is the first receive signal for the acoustic wave generated by a first transmit signal $x_0$, $y_1^s$ is the first receive signal for the acoustic wave generated by a second transmit signal $x_1$, $y_0^r$ is the second receive signal for the acoustic wave generated by a first transmit signal $x_0$ in the other propagation direction, and $y_1^r$ is the second receive signal for the acoustic wave generated by a second transmit signal $x_1$ in the other propagation direction.

15. The method according to claim 13, wherein a starting value $\hat{t}_0$ is specified for the runtime calculation by means of at least one signal envelope of a pair of receive signals $y_0^r$, $y_1^r$; $y_0^s$, $y_1^s$, wherein the receive signals $y_0^r$, $y_0^r$; $y_0^s$, $y_1^s$ of the receive signal pair originate from different transmit signals $x_0$, $x_1$ but from acoustic waves propagated in the same propagation direction.

16. The method according to claim 15, wherein a signal envelope $y_{huel}$ is given by the following formula $$y_{huel} = \sqrt{y_0^2 + y_1^2}$$

wherein:
- $y_0$ is a first receive signal for the acoustic wave generated by a first transmit signal $x_0$, and
- $y_1$ is a second receive signal for the acoustic wave generated by a second transmit signal $x_1$.

17. The method according to claim 12, wherein:
- by means of the determined absolute runtime $t_0$ a flow velocity $v_m$ of a flowing medium is determined and the acoustic waves are generated by the transmit signals $x_0$, $x_1$ such that first acoustic waves propagate through the medium along a first propagation direction in flow direction of the medium and second acoustic waves propagate through the medium along a second propagation direction against the flow direction of the medium, and
- by means of the determined absolute runtime $t_0$ a proportionality factor is calculated and with the proportionality factor and with a determined runtime difference $\Delta t$, in particular with a runtime difference $\Delta t$ determined by a method of claim 1, between at least one first and one second acoustic wave, which have at least partly propagated through the flowing medium along different propagation directions, a flow velocity $v_m$ is determined.

18. The method according to claim 1, wherein when determining several values for runtime differences $\Delta t$ of a plurality of acoustic waves, averaging and/or integrating the determined runtime differences $\Delta t$ is carried out.

19. The method according to claim 1, wherein a sound velocity, a concentration, a density, a temperature, a filling level of the medium in an interior space, a thickness of a wall adjoining the medium and/or a distance of two wall portions adjoining the medium is determined by means of a determined runtime difference $\Delta t$.

20. A device for determining physical and/or chemical properties of a medium comprising:
- an acoustic waveguide which includes an interior space to be filled with the medium,
- at least two transmitters which each are formed and provided for the generation of two first acoustic waves and two second acoustic waves in the waveguide by a transmit signal $x_0$, $x_1$ of the transmitter, so that a generated acoustic wave propagates along the waveguide and at least partly through the medium,
- at least two receivers which are spatially spaced from each other along the waveguide and each are formed and provided for the generation of a first or second receive signal $y_0^r$, $y_1^r$; $y_0^s$, $y_1^s$ for first or second acoustic waves reaching the respective receiver, wherein first acoustic waves propagate along a first propagation direction and, for this purpose, first receive signals $y_0^r$, $y_1^r$ are generated at a receiver and second acoustic waves each propagate along a second propagation direction different from the first propagation direction and, for this purpose, second receive signals $y_0^s$, $y_1^s$ are generated at a receiver, and
- a signal processing device, by means of which from the receive signals $y_0^r$, $y_1^r$; $y_0^s$, $y_1^s$, a runtime difference $\Delta t$ between received first and second acoustic waves is determined, and which is formed and provided to determine physical and/or chemical properties of the medium with a determined runtime difference ($\Delta t$),
- the transmitters of the device are formed and provided to each generate first and second acoustic waves with two different transmit signals $x_0$, $x_1$ of substantially the same fundamental frequency f and specified phase offset to each other, so that in the first propagation direction two distinguishable first receive signals $y_0^r$, $y_0^s$ and in the second propagation direction two distinguishable second receive signals, $y_1^r$; $y_1^s$ are generated by the receivers of the device, and
- the signal processing device is formed and provided to determine a runtime difference $\Delta t$ by the four receive signals $y_0^r$, $y_1^r$; $y_0^s$, $y_1^s$ of which two receive signals $y_0^r$, $y_0^s$ result from first and second acoustic waves generated by a first transmit signal $x_0$ of the two different transmit signals $x_0$, $x_1$ and two receive signals $y_1^r$, $y_1^s$ result from first and second acoustic waves generated by a second transmit signal $x_1$ of the two different transmit signals $x_0$, $x_1$.

21. The device according to claim 20, wherein the transmitters are formed and provided to generate surface acoustic waves in the waveguide.

22. The device according to claim 20, wherein the device is formed and provided for the determination of a flow velocity $v_m$ of a medium flowing through the interior space of the waveguide.

23. The device according to claim 20, wherein the signal processing device includes means for the multiplication of analog receive signals $y_0^r$, $y_1^r$; $y_0^s$, $y_1^s$ and means for the subsequent calculation of a runtime difference $\Delta t$ from digitized signals or means for digitizing the receive signals $y_0^r$, $y_1^r$; $y_0^s$, $y_1^s$ and means for the subsequent multiplication of digitized receive signals for the calculation of a runtime difference $\Delta t$.

24. The device according to claim 20, wherein the fundamental frequency f of the two transmit signals $x_0$, $x_1$ is variable.

25. The device according to claim 20, wherein the phase offset of the two transmit signals $x_0$, $x_1$ is variable between 45° and 135°, in particular is 90°.

26. The method according to claim 12, wherein when determining several values for absolute runtimes $t_0$ of a plurality of acoustic waves, averaging and/or integrating the determined absolute runtimes $t_0$ is carried out.

27. The method according to claim 12, wherein a sound velocity, a concentration, a density, a temperature, a filling level of the medium in an interior space, a thickness of a wall adjoining the medium and/or a distance of two wall portions adjoining the medium is determined by means of a determined absolute runtime $t_0$.

* * * * *